US00RE35129E

United States Patent [19]

Pethica et al.

[11] E Patent Number: Re. 35,129

[45] Reissued Date of Patent: Dec. 19, 1995

[54] OPTIMIZATION OF BONE FORMATION AT CATHODES

[75] Inventors: Brian A. Pethica, Upper Montclair, N.J.; James M. Devine, Lower Burrell, Pa.; Anthony J. Varrichio, Flanders, N.J.

[73] Assignee: Electro-Biology, Inc., Parsippany, N.J.

[21] Appl. No.: 138,230

[22] Filed: Oct. 15, 1993

Related U.S. Patent Documents

Reissue of:

[64] Patent No.: 5,056,518
Issued: Oct. 15, 1991
Appl. No.: 547,821
Filed: Jul. 2, 1990

[51] Int. Cl.[6] ..... A61N 1/00

[52] U.S. Cl. ..... 607/2; 607/51; 607/52

[58] Field of Search ..... 607/2, 3, 50, 51, 607/52, 61, 62, 66

[56] References Cited

U.S. PATENT DOCUMENTS

| | | |
|---|---|---|
| 3,842,841 | 10/1974 | Brighton et al. . |
| 3,848,608 | 11/1974 | Leonard . |
| 4,026,304 | 5/1977 | Levy . |
| 4,333,469 | 6/1982 | Jeffcoat et al. . |
| 4,430,999 | 2/1984 | Brighton et al. . |
| 4,442,846 | 4/1984 | Brighton et al. . |
| 4,506,674 | 3/1985 | Brighton et al. . |
| 4,509,520 | 4/1985 | Dugot . |
| 4,519,394 | 5/1985 | Black et al. . |
| 4,620,543 | 11/1986 | Heppenstall et al. . |
| 4,889,111 | 12/1989 | Ben-Dov et al. . |

OTHER PUBLICATIONS

Brighton, Carl T. et al., "Electrical Stimulation and Oxygen Tension," *Annals N.Y. Acad. Sci.* 238:314–320 (1974).

Brighton, Carl T. et al., "Cathodic Oxygen Consumption and Electrically Induced Osteogenesis," *Clin. Orthop. Rel. Res.* 107:277–282 (1975).

Spadaro, Joseph A., "Bioelectrochemical studies of Implantable Bone Stimulation Electrodes," *Bioelectrochem. Bioenergetics* 5:232–238 (1978).

Spadaro, Joseph A., "Electrical Osteogenesis—Role of the Electrode Material," In: Electrical Properties of Bone and Cartilage. Experimental Effects and Clinical Applications, Brighton, Black and Pollack, eds., Grune and Stratton, New York, 189–196 (1979).

Black, Jonathan et al., "Mechanisms of Stimulation of Osteogenesis by Direct Current," In: Electrical Properties of Bone and Cartilage. Experimental Effects and Clinical Application. Brighton, Black and Pollack, eds., Grune and Stratton, New York, 215–224 (1979).

Brighton, C. T., "Present and Future of Electrically Induced Osteogenesis," In: *Clinical Trends In Orthopaedics* Ed: Straub and Wilson, Jr., Thieme–Stratton, N.Y., 1–15 (1982).

Baranowski, Thomas J. et al., "Microenvironmental Changes Associated With Electrical Stimulation of Osteogenesis by Direct Current", *Trans. Bioelectrical Repair Growth Soc.* 2:47 (1982).

Baranowski, Thomas J. et al., "Mircroenvironmental Changes and Electrodic Potentials Associated With Electrical Stimulation of Osteogenesis by Direct Current," *Trans. Orthop. Res. Soc.* 8:258 2:47 (1983).

(List continued on next page.)

*Primary Examiner*—George Manuel
*Attorney, Agent, or Firm*—Woodard, Emhardt, Naughton, Moriarty & McNett

[57] ABSTRACT

A method including applying varying signals to a first electrode at the tissue site and a second electrode remote from the tissue site and monitoring the results to determine a distinctive transition in the current-voltage characteristics of the electrode pair. A signal is then selected and applied to the electrodes to operate beyond the transition. Periodically, a varying signal is applied to the electrodes and the monitoring process reperformed to determine a new transition and an appropriate signal is selected to operate beyond the transition.

24 Claims, 2 Drawing Sheets

OTHER PUBLICATIONS

Baranowski, Thomas J. et al., "The Role of Cathodic Potential in Electrical Stimulation of Osteogenesis by Direct Current" *Trans. Orthop. Res. Soc.* 8:352 (1983).

Baranowski, Thomas J. et al., "The Role of Cathodic Potential in Electrical Stimulation of Osteogenesis by Direct Current," *Trans. Bioelectrical Repair Growth Soc.* 3:34 (1983).

Baranowski, Thomas J., Jr., "Electrical Stimulation of Osteogenesis by Direct Current: Electrochemically–Mediated Microenvironmental Alterations," Ph.D. Thesis, University of Pennsylvania, Philadelphia, Pa., title page, pp. 62–72, 87–90, 211, 213–217, 233, 244–245 (1983).

Dymecki, S. M. et al., "The Cathodic Potential Dose–response Relationship for Medullary Osteogenesis with Stainless Steel Electrodes," *Trans. Bioelectrical Repair Growth Soc.* 4:29 (1984).

Black, Jonathan et al., "Electrochemical Aspects of d.c. Stimulation of Osteogenesis," Bioelectrochem. Bioenergetics 12:323–327 (1984).

Baranowski, Thomas J. et al., "The Mechanism of Faradic Stimulation of Osteogenesis," In: "Mechanistic Approaches to Interactions of Electric and Electromagnetic Fields with Living Systems," M. Blank and E. Findle, eds., Plenum Publishing Corp., New York, 399–416 (1987).

OPTIMIZATION OF BONE FORMATION AT CATHODES

Matter enclosed in heavy brackets [ ] appears in the original patent but forms no part of this reissue specification; matter printed in italics indicates the additions made by reissue.

BACKGROUND AND SUMMARY OF THE INVENTION

The present invention relates generally to electrically-induced osteogenesis and more specifically to an improved method and apparatus for optimizing stimulated osteogenesis.

It is known in the prior art to apply a cathode of metal such as platinum (Pt), titanium (Ti) or stainless steel at a bone site and an anode at a skin or tissue location near the cathode implant. The signal is applied to pass currents between the anode and cathode. Bone formation is said to be particularly favorable at 20 microamperes for single or multiple cathodes as described in U.S. Pat. No. 3,842,841 to Brighton, et al.

More recently, it has been reported in U.S. Pat. No. 4,519,394 to Black, et al that optimum bone formation is assisted by maintaining a current in the range of 0.1 to 100 microamperes per cathode port and maintaining the cathode port at a voltage substantially constant in the range of 1.0 to 1.26 volts relative to a silver-silver chloride (Ag/AgCl) reference electrode implanted or contacting body tissue. As indicated in FIG. 1 this is a three electrode system including a percutaneous or implanted cathode 18 having a port 20 positioned at a tissue site 12 of a bone 10. A transcutaneous anode 22 may be placed on the skin 16 or fully implanted in muscle or other convenient tissue. A percutaneous or implanted reference electrode 30 having a port 32 is inserted into the living tissue 14 at a point remote from the cathode and anode locations.

The current between cathodes of materials such as stainless steel, platinum, titanium or carbon and an appropriately chosen anode rises slowly with applied voltage until a voltage zone is reached at which the current increases more rapidly for small increases in voltage. This transition region ("knee") of the current-voltage characteristic or curve corresponds with the onset of chemical reactions such as oxygen reduction and hydroxide ion formation in the region of the cathode. Typically the knee occurs at an inter-electrode voltage of about 2.4 volts in physiological conditions for anode-cathode pairs such as stainless steel-stainless steel. The position of the knee also depends on tissue impedance (which changes over time) and electrode position, among other variables.

It is also known from animal experiments that bone accretion occurs at the cathode and that overly large currents cause bone loss and necrosis due to local formation of amounts of electrode reaction Products in excess of the ability of the tissue region to absorb and disperse them. There is also evidence that with particular cathodes such as stainless steel or titanium, the entire current may pass through a region close to the end of the insulation of the lead accessing the treatment site. Correspondingly, the finding in animals that 20 microamperes is optimal for the tested cathodes and cathode geometries will not describe optimum stimulation for other cathodes and geometries. Furthermore, the prior methods discussed above for maintaining the cathode voltage in a fixed range relative to a reference electrode does not necessarily optimize the voltage-current relationships with respect to the growth process and have required three electrodes.

Thus it is an object of the present invention to provide a two electrode system which provides an optimization of the current-voltage for an osteogenic stimulation.

Another object of the present invention is to provide an apparatus and method for optimising osteogenic stimulation which adapts for variation in the tissue impedance and cathode properties over time.

These and other objects are achieved by applying varying signals to a first electrode at the tissue site and a second electrode remote from the tissue site and monitoring the results to determine a distinctive transition (knee) in the current-voltage characteristics of the pair of electrodes. A signal is then selected and applied to the electrodes to operate beyond the transition. Periodically, varying signals are applied to the two electrodes and the monitoring process reperformed to determine a new transition and the appropriate signal is selected to operate beyond the transition. The current between the electrodes is typically between 10 and 50 microamps and an appropriate voltage is selected to operate beyond the transition. In some tissue repair situations it will be useful to use more than one cathode implanted in separate positions within the repair region, and each cathode may be optimised independently as described for single cathodes. In other circumstances a branched or multiport cathode may be convenient, and currents typically between 10 and 50 microamps per branch or port may be chosen at potentials beyond the transition as determined for the assembly.

Other objects, advantages and novel features of the present invention will become apparent from the following detailed description of the invention when considered in conjunction with the accompanying drawings.

DETAILED DESCRIPTION OF THE DRAWINGS

There is evidence that a voltage optimum exists for bone formation at an inert metal cathode and there is also evidence of an optimum current for a given electrode. The two optima may be fairly close together for cathodes of the form used to date by selecting an appropriate anode material and geometry (electrode length, diameter and folding). The present invention, for the optimization of both the current and voltage, is substantially independent of the materials chosen and number of ports and is capable of adapting to changes in cathode geometry and of the impedance at the tissue site.

Figure 1:
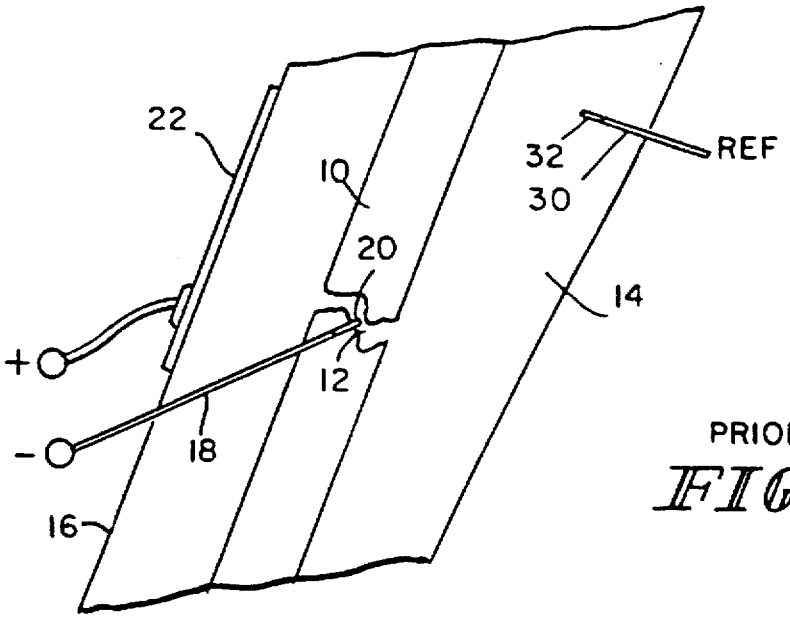
PRIOR ART FIG. 1
FIG. 1 is a side view of a prior art osteogenesis electrode arrangement.
Figure 2A:
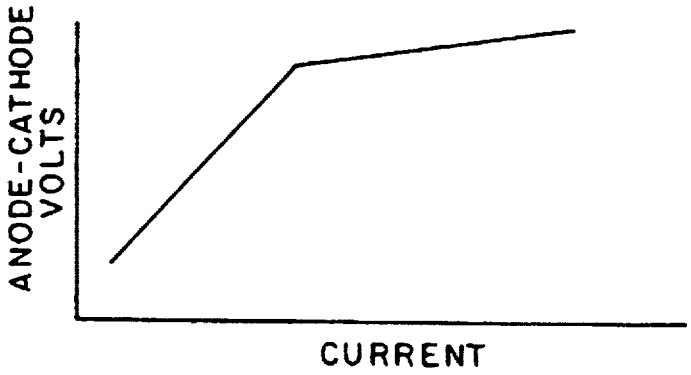
FIG. 2a is a typical graph of the current-voltage characteristics of an anode and cathode pair.
Figure 2B:
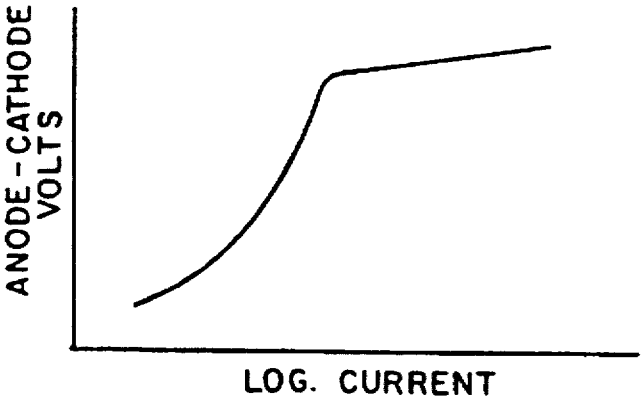
FIG. 2b shows the graph of FIG. 2a within the current shown in a logarithmic scale.

Referring to the graphs of FIG. 2a and 2b, the voltage applied between the anode and cathode has a substantial and definite rise as the current increases until a narrow region is reached beyond which the current increases rather rapidly for small increments of the applied voltage. This change in trend is here described as a transition or knee, corresponding with the onset of chemical reactions such as oxygen reduction and hydroxide ion formation in the region of the cathode.

The present invention has determined that optimum parameters for current-voltage are likely to be at potentials a little above the knee. The present invention monitors the applied voltage difference between the anode and cathode for various currents to determine the knee of the resulting curves.

Over a period of time, the impedance and composition of the region being treated may change with progression of healing. Thus the position of the knee on a current-voltage characteristic shifts with time and must be adjusted to maintain the current-voltage characteristic beyond the knee.

Figure 3:
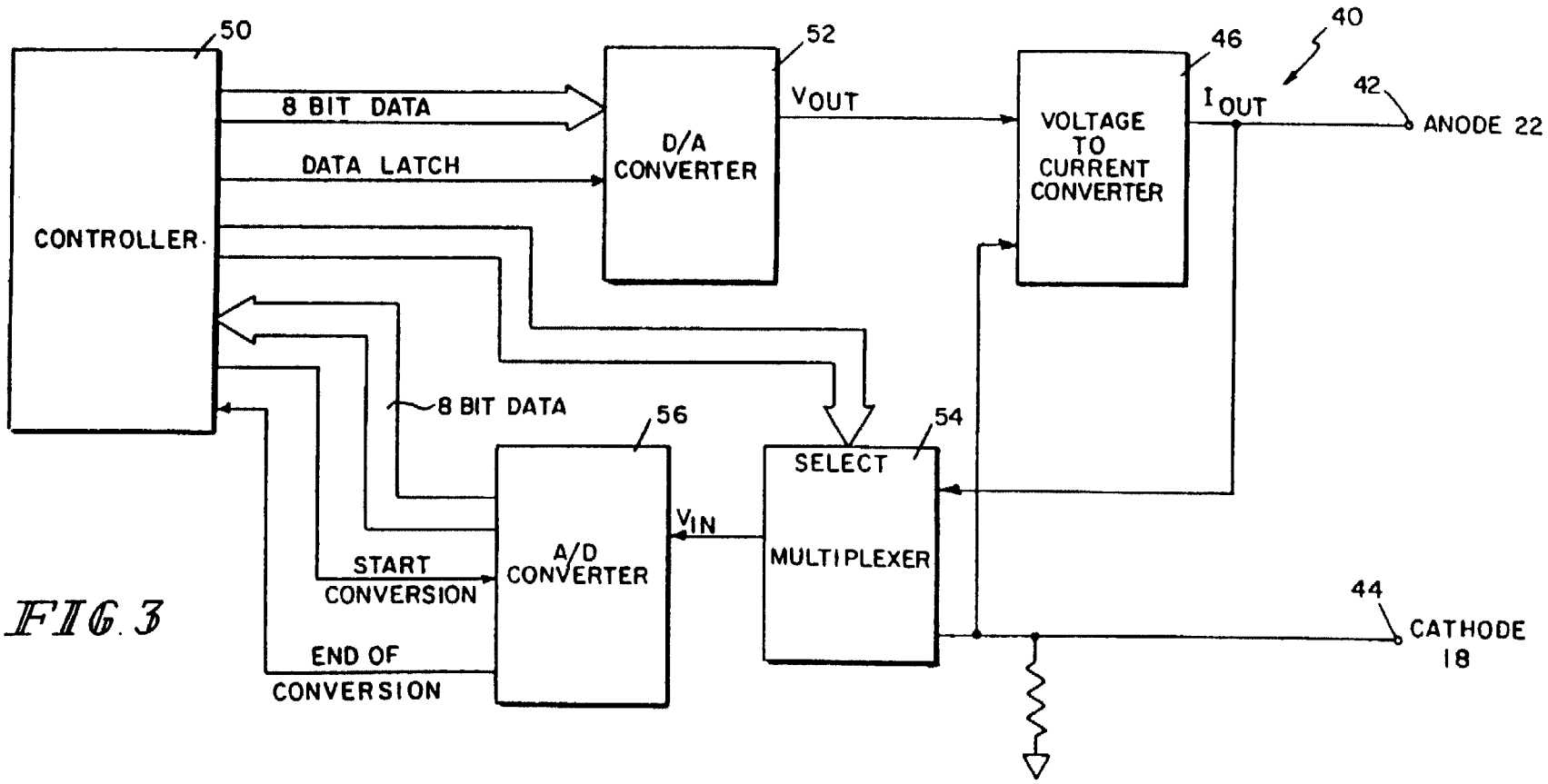
FIG. 3 is a block diagram of a osteogenic stimulator according to the principles of the present invention.

A system that is illustrated in FIG. 3 includes an anode port 42 and a cathode port 44 connectable to the anode 22 and cathode 18 with the cathode being at the tissue site. A controller 50, for example a microcomputer, provides a digital signal to digital to analog device 52 whose output is an analog voltage. This voltage is applied to the voltage/current converter 46 which provides an output current to the anode terminal 42. The anode terminal 42 and cathode terminal 44 are connected to multiplexer 54 which provides, selectively, the voltage at the anode or the cathode to analog to digital converter 56. The output of the A/D converter 56 is a digital signal provided back to the controller 50.

The process is carried out by providing varying signals to the ports 42 and 44 to produce the varying current-voltage characteristic graph. Once the knee of the curve is determined for that period of time, the voltage and current are then set to operate beyond the knee. Periodically, for example, every twelve hours, the process is repeated to determine the new current-voltage characteristic graph and then selecting an appropriate voltage/current characteristic to operate beyond the knee.

This process is carried out by the controller 50 supplying increasing values of voltage to the voltage to current converter 46 which provides increasing values of current to the anode electrode 42. Between each value of voltage provided to the D/A converter 52, the controller 50 reads the cathode and anode voltage with respect to an internal ground by controlling the multiplexer 54 and the A/D converter 56. The controller 50 will then compute the change of voltage per change of current and determined the decreased in change of voltage per change of current step to determine the existence of the knee. Once the knee has been determined, the controller 50 provides an appropriate voltage through the D/A converter 52 to set the appropriate current to the anode port 42 through the voltage to current converter 46.

The controller 50 has an internal timer which periodically reinvestigates the location of the knee and varies the appropriate signal being sent to the electrode. A typical example for the controller 50 would be a microcomputer 68HC805 by Motorola. The voltage to current converter may simply be an operational amplifier receiving on the positive terminal the output of the D/A converter 52 and on the minus terminal the feedback signal from the cathode port 44.

Although an automatic system is illustrated in FIG. 3, the process of the present invention may also be carried out with a manual system. A variable voltage may be provide as an input to the voltage to current converter 46 and the output from the anode port 42 and cathode port 44 may be provided to a monitor which would display the voltage-current characteristics. Thus, an operator can vary the input voltage and determine visually the location of the knee and thereby set the appropriate signal to achieve the desired operating characteristics. Periodically, the operator would reperform this process by changing the voltage input to the voltage to current converter 46 to redetermine the location of the knee and thereby set an appropriate voltage input.

Typically, the current range of operation is in the 10 to 50 microamperes range. In some tissue repair situations it will be useful to use more than one cathode implanted in separate positions within the repair region, and each cathode may be optimised independently as described for single cathodes. In other circumstances a branched or multiport cathode may be convenient, and currents typically between 10 and 50 microamps per branch or port may be chosen at potentials beyond the transition as determined for the assembly.

The cathode may, per example, be stainless steel, titanium or a carbon cathode whereas the anode may be for example, stainless steel mesh or a platimum-plated titanium or other inert metals or other tissue-compatable electrodes such as salt bridge or conducting polymers. The cathode or anode may be attached to insulated leads. It should also be noted that the anode may be placed transcutaneous, percutaneous or totally implanted and that the cathode may be placed transcutaneously or fully implanted. Insulated leads which may be attached to the anode or cathode may also be placed percutaneously or totally implanted. The stimulator or signal generator may be totally implanted or may be external and connected to the electrodes by leads or inductivity. It should also be noted that the present invention is not to be limited to fractures but to any bone growth process including spinal fusion, for example.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A method of stimulating osteogenesis or other tissue repair processes at a tissue site within a living body comprising:

locating a first electrode at said tissue site within the living body;

coupling a second electrode to said living body remote from said tissue site;

applying various signal levels to said first and second electrodes and monitoring the resulting current flows between the electrodes to determine a current-voltage characteristic of said electrodes;

identifying a voltage signal level at which a distinctive transition occurs in said current-voltage characteristic; and applying a voltage signal level to said electrodes to cause the electrodes to operate at a point on the current-voltage characteristic which is just beyond the point at which said transition occurs.

2. A method according to claim 1, including periodically applying said signal levels to said electrodes and monitoring the resulting current flow between the electrodes to redetermine the location along said current voltage characteristic of said transition point, and modifying said voltage signal applied to said electrodes to cause the electrodes to operate just beyond said newly determined transition point.

3. A method according to claim 1, wherein said electrodes are operated at a current level between 10 and 50 microamperes.

4. A method according to claim 1, wherein said first electrode is a cathode and said second electrode is an anode.

5. A method according to claim 1, wherein said second electrode is percutaneous.

6. A method according to claim 1, wherein said second electrode is fully implanted.

7. A method according to claim 1, wherein said second electrode is located transcutaneous.

8. A method according to claim 1, including:

locating a plurality of first electrodes at said tissue site;

applying said signal levels to said plurality of first electrodes and said second electrodes and monitoring the resulting current flows to determine the voltage signal level associated with said distinctive transition for each of said first electrodes; and applying a voltage signal level to each of said first electrodes to cause each of said electrodes to operate just beyond its respective transition point.

9. A method according to claim 8, wherein each of first electrodes includes a plurality of conducting ports at said tissue site; and wherein said voltage signal level is applied to said electrodes such that each conducting port carries a current between 10 and 50 microamps.

10. A method according to claim 1, wherein:

said first electrode includes a plurality of conducting ports at said tissue site; and wherein said signal level is applied to said electrodes such that each conducting port carries a current between 10 and 50 microamps.

11. An apparatus for stimulating osteogenesis or other tissue repair processes at a tissue site in living tissue comprising:

a first electrode adapted to be positioned at said tissue site within the living body;

a second electrode adapted to be positioned in electrical contact with said living body;

signal means connected to said first and second electrodes for applying various voltage signal levels to said first and second electrodes and for monitoring resulting current flows between the electrodes to determine a current-voltage characteristic of said electrodes, and for applying a voltage signal level to the electrodes to cause the electrodes to operate at a point along the current-voltage characteristic which is just beyond the point at which a distinctive transition in said characteristic occurs.

12. An apparatus according to claim 11, wherein said signal means further comprises:

monitor means for monitoring said current-voltage characteristic and for recognizing changes in the point at which the distinctive transition occurs;

control means for causing said signal means to maintain the operation of the electrodes at a point which is just beyond the point at which the changed transition occurs.

13. An apparatus according to claim 12, wherein said monitor means includes timing means for periodically causing said monitor means to recognize changes in the point at which the transition occurs, and for causing said signal means to maintain the operation of the electrodes at a point which is just beyond the point at which the changed transition occurs.

14. An apparatus according to claim 11, wherein said signal means provides a current of between 10 to 50 microamperes.

15. An apparatus according to claim 11, wherein said first electrode is a cathode and said second electrode is an anode.

16. An apparatus according to claim 11, wherein said first electrode is a percutaneous electrode and said second electrode is a transcutaneous electrode.

17. An apparatus according to claim 11, wherein said first electrode is a percutaneous electrode and said second electrode is a percutaneous electrode.

18. An apparatus according to claim 11, wherein said first and second electrodes are totally implantable electrodes.

19. An apparatus according to claim 18, wherein said signal means is totally implantable.

20. An apparatus according to claim 11, further comprising a plurality of first electrodes adapted to be positioned at said tissue site; and wherein said signal means applies a voltage signal level to each of said first electrodes to cause the electrodes to operate at a point along its respective current-voltage characteristic which is just beyond its distinctive transition point.

*21. A method of dynamically determining an operating point for stimulation of osteogenesis or other tissue repair processes at a tissue site within a living body comprising:*

*locating a first electrode at said tissue site within the living body;*

*coupling a second electrode to said living body remote from said tissue site;*

*applying various signal levels to said first and second electrodes and monitoring the resulting current flows between the electrodes to determine a current-voltage characteristic of said electrodes;*

*identifying a voltage signal level at which a distinctive transition occurs in said current-voltage characteristic; and*

*periodically applying said signal levels to said electrodes and monitoring the resulting current flow between the electrodes to re-determine the location along said current voltage characteristic of said transition point.*

*22. A method of stimulating osteogenesis or other tissue repair processes at a tissue site within a living body comprising:*

*locating a first electrode at said tissue site within the living body;*

*coupling a second electrode to said living body remote from said tissue site;*

*applying various signal levels to said first and second electrodes and monitoring the resulting current flows between the electrodes to determine a current-voltage characteristic of said electrodes;*

*identifying a voltage signal level at which a distinctive transition occurs in said current-voltage characteristic;*

*applying a voltage signal level to said electrodes to cause the electrodes to operate about a point on the current-voltage characteristic at which said transition occurs;*

*periodically applying said signal levels to said electrodes and monitoring the resulting current flow between the electrodes to re-determine the location along said current voltage characteristic of said transition point; and*

*modifying said voltage signal applied to said electrodes to cause the electrodes to operate about said newly determined transition point.*

*23. An apparatus for dynamically determining an operating point for stimulation of osteogenesis or other tissue repair processes at a tissue site in living tissue comprising:*

*a first electrode adapted to be positioned at said tissue site within the living body;*

*a second electrode adapted to be positioned in electrical contact with said living body;*

*signal means connected to said first and second electrodes for applying various voltage signal levels to said first and second electrodes and for monitoring resulting current flows between the electrodes to determine a current-voltage characteristic of said electrodes, said signal means including monitor means for monitoring said current-voltage characteristic and for recognizing changes in the point at which the distinctive transition occurs.*

*24. An apparatus for stimulating osteogenesis or other tissue repair processes at a tissue site in living tissue comprising:*

*a first electrode adapted to be positioned at said tissue site within the living body;*

*a second electrode adapted to be positioned in electrical contact with said living body; and*

*signal means connected to said first and second electrodes for applying various voltage signal levels to said first and second electrodes and for monitoring resulting current flows between the electrodes to determine a current-voltage characteristic of said electrodes, and for applying a voltage signal level to the electrodes to cause the electrodes to operated about a point along the current-voltage characteristic at which a distinctive transition in said characteristic occurs, said signal means including monitor means for monitoring said current-voltage characteristic and for recognizing changes in the point at which the distinctive transition occurs, and control means for causing said signal means to maintain the operation of the electrodes about the point at which the changed transition occurs.*

* * * * *